United States Patent
Zou

(10) Patent No.: US 11,925,460 B2
(45) Date of Patent: Mar. 12, 2024

(54) BIOCOMPATIBILITY COATING FOR CONTINUOUS ANALYTE MEASUREMENT

(71) Applicant: Roche Diabetes Care, Inc., Indianapolis, IN (US)

(72) Inventor: Peng Zou, Ludwigshafen am Rhein (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 85 days.

(21) Appl. No.: 17/003,258

(22) Filed: Aug. 26, 2020

(65) Prior Publication Data
US 2020/0390376 A1 Dec. 17, 2020

Related U.S. Application Data

(63) Continuation of application No. PCT/EP2019/054657, filed on Feb. 26, 2019.

(30) Foreign Application Priority Data

Feb. 28, 2018 (EP) .................................... 18159263

(51) Int. Cl.
*A61B 5/145* (2006.01)
*G01N 33/543* (2006.01)
*A61B 5/1486* (2006.01)

(52) U.S. Cl.
CPC ...... *A61B 5/14503* (2013.01); *A61B 5/14532* (2013.01); *A61B 5/14546* (2013.01); *G01N 33/54393* (2013.01); *A61B 5/14865* (2013.01)

(58) Field of Classification Search
CPC ............ A61B 5/14503; A61B 5/14532; A61B 5/14546; A61B 5/14865; G01N 33/54393
See application file for complete search history.

(56) References Cited

U.S. PATENT DOCUMENTS

| 5,206,147 A | 4/1993 | Hoenes |
| 5,240,860 A | 8/1993 | Hoenes et al. |

(Continued)

FOREIGN PATENT DOCUMENTS

| CN | 101184851 A | 5/2008 |
| EP | 0 354 441 A2 | 2/1990 |

(Continued)

OTHER PUBLICATIONS

Bunte, Christine, et al. "Enzyme containing redox polymer networks for biosensors or biofuel cells: a photochemical approach." Langmuir 26.8: 6019-6027. (Year: 2010).*

(Continued)

*Primary Examiner* — Eric J Messersmith
(74) *Attorney, Agent, or Firm* — Bose McKinnney & Evans LLP

(57) ABSTRACT

A biosensor for determining an analyte is disclosed. The sensor has a sensor module covered at least partially by a biocompatibility layer. The biocompatibility layer has a polymer having —CO—NR$^1$R$^2$ side groups, wherein R$^1$ and R$^2$ are independently selected from —H and $C_1$ to $C_6$ alkyl. A method for producing the biosensor, as well as to uses and methods of using related to the biosensor, are also disclosed.

23 Claims, 5 Drawing Sheets

(56) References Cited

U.S. PATENT DOCUMENTS

| | | | |
|---|---|---|---|
| 5,385,846 | A | 1/1995 | Kuhn et al. |
| 5,997,817 | A | 12/1999 | Crismore et al. |
| 6,036,919 | A | 3/2000 | Thym et al. |
| RE42,953 | E | 11/2011 | Crismore et al. |
| 2005/0023152 | A1 | 2/2005 | Surridge et al. |
| 2006/0198864 | A1 | 9/2006 | Shults et al. |
| 2006/0275860 | A1 | 12/2006 | Kjaer et al. |
| 2008/0179187 | A1 | 7/2008 | Ouyang et al. |
| 2008/0213809 | A1 | 9/2008 | Heindl et al. |
| 2011/0143416 | A1 | 6/2011 | Horn et al. |
| 2014/0012115 | A1 | 1/2014 | Li et al. |

FOREIGN PATENT DOCUMENTS

| | | |
|---|---|---|
| EP | 0 431 456 A1 | 6/1991 |
| EP | 0 821 234 A2 | 1/1998 |
| EP | 0 974 303 A1 | 1/2000 |
| EP | 2 583 699 A1 | 4/2013 |
| EP | 3 263 712 A1 | 1/2018 |
| RU | 2 485 887 C2 | 6/2013 |
| WO | WO 2007/012494 A1 | 2/2007 |
| WO | WO 2009/103540 A1 | 8/2009 |
| WO | WO 2011/012269 A2 | 2/2011 |
| WO | WO 2011/012270 A1 | 2/2011 |
| WO | WO 2011/012271 A2 | 2/2011 |
| WO | WO 2012/035302 A1 | 3/2012 |
| WO | WO 2015/005953 A1 | 1/2015 |
| WO | WO 2017/189764 A1 | 11/2017 |
| WO | WO 2017/214173 A1 | 12/2017 |

OTHER PUBLICATIONS

Wang, Ning, et al. "Electrospun fibro-porous polyurethane coatings for implantable glucose biosensors." Biomaterials 34.4: 888-901. (Year: 2013).*

Prucker O, Brandstetter T, Rühe J. Surface-attached hydrogel coatings via C,H-insertion crosslinking for biomedical and bioanalytical applications (Review). Biointerphases. Dec. 8, 2017;13(1):010801. doi: 10.1116/1.4999786. PMID: 29221372. (Year: 2017).*

International Search Report and Written Opinion of the International Searching Authority, PCT/EP2019/054657, dated Mar. 21, 2019, 15 pages.

Hönes et al., The Technology Behind Glucose Meters: Test Strips, Diabetes Technology and Therapeutics, vol. 10, Supplement 1, 2008, pp. 10-26.

Hu et al., Antifouling Zwitterionic Coating via Electrochemically Mediated Atom Transfer Radical Polymerization on Enzyme-Based Glucose Sensors for Long-Time Stability in 37° C. Serum, Langmuir, vol. 32, No. 45, Nov. 3, 2016, pp. 11763-11770.

Krishnan et al., Advances in Polymers for Anti-Biofouling Surfaces, Journal of Materials Chemistry, Issue 29, 2008, 18, pp. 3405-3413.

Wisniewski et al., Characterization of Implantable Biosensor Membrane Biofouling, Fresnius Journal of Analytical Chemistry, vol. 366, Nos. 6-7, Mar. 30, 2000, pp. 611-621.

Wang et al., Electrospun Fibro-Porous Polyurethane Coatings for Implantable Glucose Biosensors, Biomaterials, vol. 34, No. 4, Jan. 1, 2013, pp. 888-901.

Yang et al., Preparation of the Antifouling Microfiltration Membranes from Poly(N,Ndimethylacrylamide) Grafted Poly(Vinylidene Fluoride) (PVDF) Powder, Journal of Materials Chemistry, vol. 21, No. 32, Jan. 1, 2011, pp. 11908-11915.

Guiseppi-Elie et al., Design of a Subcutaneous Implantable Biochip for Monitoring of Glucose and Lactate, IEEE Sensors Journal, vol. 5, No. 3, Jun. 1, 2005, pp. 345-355.

Chen et al., Current and Emerging Technology for Continuous Glucose Monitoring, Sensors, vol. 17, No. 12, Jan. 19, 2017, 19 pages.

Hadler et al., Polymer Coatings of Cochlear Implant Electrode Surface—An Option for Improving Electrode-Nerve-Interface by Blocking Fibroblast Overgrowth, PLoS One, vol. 11, No. 7, Jul. 8, 2016, 22 pages.

Liu et al., Amino Acid-Based Zwitterionic Poly(Serine Methacrylate) as an Antifouling Material, Biomacromolecules, vol. 14, No. 1, Jan. 14, 2013, pp. 226-231.

Harding et al., Combating Medical Device Fouling, Trends in Biotechnology, vol. 32, No. 3, Mar. 1, 2014, pp. 140-146.

Utrata-Wesolek, Antifouling Surfaces in Medical Application, Polimery, vol. 58, No. 9, Jan. 1, 2013, pp. 685-695.

Bunte et al., Enzyme Containing Redox Polymer Networks for Biosensors or Biofuel Cells: A Photochemical Approach, Langmuir, 2010, vol. 26, No. 8, pp. 6019-6027.

* cited by examiner

BIOCOMPATIBILITY COATING FOR CONTINUOUS ANALYTE MEASUREMENT

RELATED APPLICATIONS

This application is a continuation of PCT/EP2019/054657, filed Feb. 26, 2019, which claims priority to EP 18 159 263.5, filed Feb. 28, 2018, the entire disclosures of which are hereby incorporated herein by reference in their entireties.

BACKGROUND

This disclosure relates to a biosensor for determining an analyte comprising a sensor module covered at least partially by a biocompatibility layer, wherein said biocompatibility layer comprises a polymer having —CO—NR$^1$R$^2$ side groups, wherein R$^1$ and R$^2$ are independently selected from —H and C$_1$ to C$_6$ alkyl. This disclosure further relates to a method for producing said biosensor, as well as to uses and methods of using related to said biosensor.

Biosensors for measuring analytes in biological fluids, in particular sensors designed for implantation, have to fulfil a variety of functions: on the one hand, the sensor must provide for specific and sensitive measurement without interference from, e.g., particular compounds of body fluids, such as cells. For this purpose, biosensors are frequently covered with membranes excluding particular compounds in order to allow access to the actual sensor module only for low molecular weight compounds. Moreover, with implanted sensors, it is preferred to have sensors which can remain in place for a long period without deterioration of the measurement, in order to spare the patient frequently exchanging the sensor. Accordingly, implanted sensors are covered with biocompatible polymers in order to avoid the body recognizing and rejecting the implanted sensor. Furthermore, a suitable biocompatible layer should prevent constituents of body fluids from being deposited on the membrane, e.g., polypeptides or cells, since this leads to a clogging of the pores of the membrane, causing an increased noise and reduced signal intensity of measurement.

In particular, it was observed that frequently a cell layer forms on implanted biosensors, which prevents the passage of molecules that cannot easily diffuse through the cell layer, including, e.g., glucose. Accordingly, it was proposed to provide a membrane interfering with the formation of the barrier cell layer and to protect sensitive regions of an implantable device from biofouling by including bioactive agents into the biointerface membrane (U.S. Publication No. 2006/0198864 A1). Moreover, biocompatible polymers such as ADAPT™ formulations have been used to improve performance of biosensors. Hu and colleagues developed an antifouling zwitterionic coating for enzyme-based biosenors (Hu et al, Langmuir, 2016, 32, 11763-11770) based on pSBMA (poly N-(3-sulfopropyl)-N-(meth-acryloxyethyl)-N, N-dimethylammonium betaine) using electrochemically induced atom transfer radical polymerization (eATRP). Krishnan and colleagues discuss a variety of polymers with anti-biofouling activity including hydrophilic PEGylated polymers, zwitterionic polymers, and polymers incorporating oligosaccharide moieties, mainly in the context of marine coatings (Krishnan et al, J. Mater. Chem., 2008, 18, 3405-3413).

Nonetheless, with currently used biocompatible polymers, e.g., implanted continuous glucose monitoring (CGM) biosensors may start to show signs of measurable fouling after a relatively short wearing time.

SUMMARY

This disclosure teaches improved means and methods for coating biosensors, avoiding at least in part the drawbacks of the prior art, in particular with regard to fouling and encapsulation processes.

Accordingly, this disclosure relates to a sensor for determining an analyte comprising a sensor module covered at least partially by a biocompatibility coating, wherein said biocompatibility coating comprises a polymer having —CO—NR$^1$R$^2$ side groups, wherein R$^1$ and R$^2$ are independently selected from —H and C$_1$ to C$_6$ alkyl.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, as used in the following, the terms "preferably," "more preferably," "most preferably," "particularly," "more particularly," "specifically," "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention.

As used herein, the term "standard conditions," if not otherwise noted, relates to IUPAC standard ambient temperature and pressure (SATP) conditions, i.e., in an embodiment, a temperature of 25° C. and an absolute pressure of 100 kPa; also in an embodiment, standard conditions include a pH of 7. Moreover, if not otherwise indicated, the term "about" relates to the indicated value with the commonly accepted technical precision in the relevant field, in an embodiment relates to the indicated value ±20%, in a further embodiment ±10%, in a further embodiment ±5%. Further, the term "essentially" indicates that deviations having influence on the indicated result or use are absent, i.e., potential deviations do not cause the indicated result to deviate by more than ±20%, in a further embodiment ±10%, in a further embodiment ±5%. Thus, "consisting essentially of" means including the components specified but excluding other components except for materials present as impurities, unavoidable materials present as a result of processes used to provide the components, and components added for a purpose other than achieving the technical effect of this disclosure. For example, a composition defined using the phrase "consisting essentially of" encompasses any known acceptable additive, excipient, diluent, carrier, and the like. In an embodiment, a composition consisting essentially of a set of components will comprise less than 5% by weight, in a further embodiment less than 3% by weight, in a further embodiment less than 1%, in a further embodiment less than 0.1% by weight of non-specified component(s).

The term "biosensor," as used herein, relates to a device comprising the means as indicated herein. The biosensor comprises at least a sensor module and a biocompatibility layer, both as specified herein below. In an embodiment, the biosensor is an implantable biosensor, in an embodiment is implantable subcutaneously. In an embodiment, the biosensor is fully implantable, i.e., the biosensor including its means for external communication is implantable, in an embodiment without requiring an opening in the skin of a subject for operation. Thus, in an embodiment, the communication by the biosensor with external devices is wireless. As will be understood by the skilled person, insertion of the biosensor may require an opening in the skin of a subject.

In an embodiment, the sensor further comprises an aperture, i.e., an opening permitting the sensor module to contact the surrounding medium, in particular a body fluid. In an embodiment, said aperture is located in the vicinity of the sensor module and the biocompatibility layer, optionally in combination with a diffusion membrane, separates the sensor module from the analysis fluid. Moreover, in particular in case the biosensor is an implantable biosensor, the biosensor comprises further electric and electronic means, including, e.g., an energy source, like a battery, and/or a communication unit for exchanging information with an external device, e.g., for reporting measured values of an analyte. Suitable means for providing energy sources and communication units are well-known in the art. In an embodiment, the biosensor further comprises a processing unit converting a detectable signal or a physical signal derived therefrom, e.g., an electric signal, into a signal which is communicated to a read-out unit, e.g., a reader. In a further embodiment, the processing unit converts the detectable signal or a physical signal derived therefrom to a measurement value, e.g., an analyte concentration. It will be understood that the aforementioned means may perform additional functions and that the biosensor may comprise further means as found appropriate by the skilled artisan.

In an embodiment, the biosensor further comprises a diffusion membrane. The term "diffusion membrane," as used herein, relates to a polymer permitting diffusion of the analyte, in particular with a thickness of from 1 µm to 100 µm, in an embodiment of from 2.5 µm to 50 µm. In an embodiment, the diffusion membrane comprises or consists of a biocompatible polymer, in particular a polymer produced by polymerizing butyl-methacrylate (BUMA) and/or 2-hydroxyethylmethacrylate (HEMA) monomers. In a further embodiment, the diffusion membrane comprises a hydrophilic polyurethane polymer (HPU). In a further embodiment, the diffusion membrane permits diffusion of the analyte, but not of high-molecular constituents comprised in an analysis fluid, e.g., a bodily fluid. Accordingly, the diffusion membrane, in an embodiment, specifically permits diffusion of molecules with a molecular weight of less than 10 kDa, in an embodiment less than 5 kDa, in a further embodiment less than 1 kDa. Thus, in an embodiment, the diffusion membrane is a semipermeable membrane, in particular a dialysis membrane, in an embodiment a biocompatible dialysis membrane.

In an embodiment, the biosensor is completely covered by the biocompatibility layer. In a further embodiment, the sensor is produced from an inert material and comprises an aperture as specified herein above, wherein said aperture is at least partly covered by the biocompatibility layer; or the aperture and/or the sensor module are at least partly covered by at least the biocompatibility layer, "at least partly covered" meaning that at least an area sufficient for measurement of the analyte to be performed is covered by the biocompatibility layer. In an embodiment, at least 25%, in a further embodiment, at least 50%, in a further embodiment at least 75%, in a further embodiment at least 90% of the area of the aperture and/or of the test field of the sensor module as specified herein below are covered by the biocompatibility membrane.

In an embodiment, the biosensor is an electrochemical biosensor; thus, the biosensor may comprise further electrical leads and contacts. In an embodiment, the biosensor comprises further electrodes, which may be electrodes having the features as described below, or may be electrodes structurally and/or functionally different therefrom. Further electrodes may, e.g., be adapted for use as a filling control, as a temperature sensor, and the like. In an embodiment, the biosensor further comprises a counter electrode, in a further embodiment further comprises a reference electrode and a counter electrode. It is known in the art that the biosensor may comprise three electrodes, of which one each is a working electrode, a counter electrode, and a reference electrode ("three-electrode setup"); or the biosensor may comprise two electrodes of which one is a working electrode and the second is a counter electrode and reference electrode ("two-electrode setup"). As indicated above, the biosensor may also comprise further electrodes. As used in the context of the present disclosure, at least the working electrode is in electrical, i.e., conductive, contact with at least a portion of a test field.

In an embodiment, the biosensor is an optical biosensor; thus, the biosensor may comprise further optical means, e.g., an illumination unit and/or an optically sensitive element, e.g., a photocell. In an embodiment, sensor module includes at least one light source for illuminating at least part of a test field as specified elsewhere herein and comprises at least one optically sensitive element adapted to determine detection light from said test field. Thus, in an embodiment, the sensor module comprises at least one light source, e.g., a light emitting diode (LED). In an embodiment, the detection light is selected from the group consisting of light reflected by the test field, light transmitted by the test field, and light emitted by the test field. In an embodiment, the optically sensitive element comprises at least one element adapted to detect light emitted by a light source and reflected and/or transmitted by a test field. Said optically sensitive element may, e.g., be a photo diode. In an embodiment, the optically sensitive element comprises at least one one-dimensional or two-dimensional matrix of optically sensitive elements, in an embodiment at least one camera chip, and in a further embodiment at least one CCD chip. In an embodiment, the optical signal is converted into an electrical signal after its detection, thus, the biosensor may comprise the further elements described herein above for an electrochemical sensor as deemed appropriate by the skilled person.

The term "sensor module," as used herein, relates to a unit comprising at least one test field generating a detectable signal in the presence of an analyte and, optionally, a signal detection unit detecting and/or transforming the detectable signal into an output signal, e.g., an electric output signal, e.g., a current, a voltage, or the like. In an embodiment, the sensor module is selected from an optical sensor module and an electrochemical sensor module as specified above. Both types of sensor module are, in principle, known in the art.

The term "detectable signal," as used herein, relates to any property of a test chemistry which changes in the presence of the analyte and which can be transferred into a physical signal of any kind. In an embodiment, the change of the measurable property and/or the signal generatable therefrom are proportional to the concentration of the analyte in the sample. In an embodiment, as described above, the measurable property is a change in color and/or in color intensity of the test chemistry, i.e., in an embodiment, a change in the absorption and/or emission spectrum of the test chemistry. Thus, in the change of the measurable property the optical property in an embodiment is selected from the group consisting of: a reflection property, in an embodiment a reflectance and/or a remission; transmission property, in an embodiment an absorption; a color; a luminescence, in an embodiment a fluorescence. Also in an embodiment, the measurable property is the concentration of a reduced or an oxidized redox compound, e.g., a mediator, as described elsewhere herein. Methods of converting the measurable property as defined above into a physical signal which can be read as a measurement value are well known in the art and are described e.g., in EP 0 821 234, EP 0 974 303, and U.S. Publication No. 2005/0023152.

In an embodiment, the measurable property is the redox state of a redox compound comprised in the test chemistry and is detected by electrochemical means, e.g., by measuring a voltage, capacity, admittance, current or any parameter deemed appropriate by the skilled person. Thus, it is also envisaged by this disclosure that the test chemistry includes a chemical reagent for reacting with the analyte to produce an electrochemical signal that represents the presence of the analyte in the sample fluid. In the case of glucose as a preferred analyte, the active components of the test chemistry will typically include an enzyme utilizing, in an embodiment specifically utilizing, glucose and, optionally, a redox mediator. In a further embodiment, said enzyme comprises at least one of glucose oxidase and glucose dehydrogenase. In an embodiment, the enzyme produces a reduced cofactor, e.g., NAD(P)H in the presence of an analyte and a mediator in turn reacts with the reduced cofactor. The mediator thereafter shuttles the redox equivalent of analyte product to the electrode surface by diffusion. There the mediator is oxidized quantitatively at a defined anodic potential and the resulting current is related to the apparent glucose concentration. In general, the preferred redox mediators are rapidly reducible and oxidizable molecules. Examples include ferricyanide, nitrosoaniline and derivatives thereof, and ferrocene and its derivatives. In another embodiment, the enzyme, e.g., glucose oxidase, produces a peroxide, in particular hydrogen peroxide, which is detected electrochemically. There are a number of reagent systems suitable for the detection of glucose, and examples comprise AC Excitation, Analyte Sensors, and Biosensor applications, U.S. Pat. Nos. 5,385,846 and 5,997,817, and U.S. (Reissue) patent application Ser. No. 10/008,788 ("Electrochemical Biosensor Test Strip"); the cNAD chemistry as described in WO 2007/012494, WO 2009/103540, WO 2011/012269, WO 2011/012270, and WO 2011/012271; and the SCV chemistry as described in EP 0 354 441, EP 0 431 456.

In another embodiment, the detection reaction implies a color change of the test chemistry or of at least a part thereof In an embodiment, the test chemistry comprises at least one enzyme, which in an embodiment directly or indirectly reacts with the analyte, in an embodiment with a high specificity, wherein, further, one or more optical indicator substances are present in the test chemistry, which perform at least one optically detectable property change when the at least one enzyme reacts with the analyte. Thus, the at least one indicator may comprise one or more dyes performing a color changing reaction indicative of the enzymatic reaction of the at least one enzyme and the analyte. An exemplary embodiment of an optical detection is disclosed, e.g., in WO 2015/005953 A1.

The term "test field," as used herein, relates to a continuous or discontinuous amount of a test chemistry, which, in an embodiment, is held by at least one carrier, such as by at least one carrier film. Thus, the test chemistry as specified elsewhere herein may form or may be comprised in one or more films or layers of the test field, and/or the test field may comprise a layer setup having one or more layers, wherein at least one of the layers comprises the test chemistry. Thus, the test field may comprise a layer setup disposed on a carrier, wherein the sample may contact the layer setup from at least one application side. In an embodiment, the test field has a multilayer setup, the multilayer setup comprising at least one detection layer having the at least one test chemistry and further comprising at least one separation layer adapted for separating off at least one particulate component contained in the body fluid, wherein the separation layer is located between the detection layer and the sample access site.

The terms "test chemistry" or "test material" refer to a substance or mixture of substances adapted to change at least one measurable property in the presence of the analyte. In an embodiment, the test material performs at least one optically or electrochemically detectable detection reaction in the presence of the analyte. In an embodiment, the test reaction is at least in part mediated by at least one enzyme, thus, in an embodiment, the test material comprises at least one enzyme adapted for performing at least one enzymatic reaction in the presence of the analyte. With regard to the test chemistry, various possibilities of designing the test chemistry are known in the art. The test chemistry is selected in respect to the analyte to be assessed.

The term "enzyme," as used herein, relates to a biological macromolecule, in particular a polypeptide, catalyzing in the presence of an analyte a chemical reaction producing or consuming a compound providing a detectable signal. In an embodiment, the enzyme is an oxidoreductase, in particular an oxidase; in a further embodiment, the enzyme produces a peroxide in the presence of an analyte, in particular produces hydrogen peroxide; thus, in an embodiment, the enzyme is a hydrogen peroxide producing oxidase, e.g., a glucose oxidase (EC 1.1.3.4), hexose oxidase (EC 1.1.3.5), cholesterol oxidase (EC 1.1.3.6), galactose oxidase (EC 1.1.3.9), alcohol oxidase (EC 1.1.3.13), L-gulonolactone oxidase (EC 1.1.3.8), NAD(P)H oxidase ($H_2O_2$-forming, EC 1.6.3.1), NADH oxidase ($H_2O_2$-forming, EC 1.6.3.3) or catalase (EC 1.11.1.6). In an embodiment, as specified elsewhere herein, the analyte is glucose. Thus, the at least one enzyme may comprise an enzyme, in an embodiment an oxidoreductase, having glucose as a substrate, in particular glucose oxidase and/or glucose dehydrogenase. In a further embodiment, the enzyme is glucose oxidase (EC 1.1.3.4). In this regard, reference may be made to the above-mentioned prior art documents. Specifically, reference may be made to J. Hoenes et al.: The Technology Behind Glucose Meters: Test Strips, Diabetes Technology & Therapeutics, Volume 10, Supplement 1, 2008, S-10 to S-26. However, other types of enzymes and/or other types of test chemistry or active components of the test chemistry may be used.

The term "biocompatibility layer," as used herein, relates to a layer, in particular an outmost layer of a biosensor or part thereof, consisting of a biocompatible material. In an embodiment, the biocompatibility layer has a thickness of from 5 nm to 100 µm, in an embodiment of from 10 nm to 1 µm. In an embodiment, the biocompatibility layer at least partly covers the test field of the sensor module, in a further embodiment at least partly covers the sensor module, in a further embodiment completely covers the portions of the sensor module not contacting the other elements of the biosensor, in a further embodiment at least partly or completely covers the biosensor. In an embodiment, the biocompatibility layer is the outmost layer of the sensor module and/or of the biosensor. Thus, in an embodiment, at least a part of the biocompatibility layer contacts a body fluid of a subject. In an embodiment, the biocompatibility layer is not diffusion-limiting for the analyte as specified elsewhere herein; in a further embodiment, the biocompatibility layer is not diffusion-limiting for small molecules having a molecular weight of less than 2,000 Da, in an embodiment less than 1000 Da. In an embodiment, the biocompatibility layer does not comprise an added enzyme, in a further embodiment, the biocompatibility layer does not comprise an added polypeptide; as will be understood by the skilled person, this does not exclude that enzyme or polypeptide molecules diffuse into the biocompatibility layer from adjacent layers, tissues, or body fluids.

The term "biocompatible material," as used herein relates to a material suitable for use with living tissue or a living system by not being or being to a reduced extent toxic, injurious, or physiologically reactive and/or causing to a reduced extent or not causing immunological rejection. In an embodiment, the biocompatible material is a material not inducing a bodily response, e.g., an inert material or a material comprising chemical compounds preventing bodily responses from occurring in the vicinity of the biocompatibility layer. In another embodiment, the biocompatible material is a material preventing cells from attaching to said biocompatibility layer. In a further embodiment, as indicated herein above, the biosensor comprises at least two layers, of which the outer layer is the layer comprising said polymer having —C(O)—$NR^1R^2$ side groups, i.e., the biocompatibility layer. In an embodiment, a second layer is a diffusion membrane as specified elsewhere herein. In an embodiment, the biocompatibility layer and the diffusion membrane are covalently linked, in an embodiment by photo-activation, via the cross-linkable side group as specified herein below.

The biocompatibility layer as disclosed herein comprises, in an embodiment consists of, a polymer having —C(O)—$NR^1R^2$ side groups, wherein $R^1$ and $R^2$ are independently selected from —H and $C_1$ to $C_6$ alkyl. Thus, in an embodiment, the polymer comprises unsubstituted amide side groups. In an embodiment, at most one of $R^1$ and $R^2$ is —H. Thus, in an embodiment, the polymer comprises mono- and/or di-N-substituted amide side groups.

As used herein, the term "alkyl" relates to a univalent side group derived from an alkane by removal of a hydrogen atom from any carbon atom. In an embodiment, the alkyl is a straight or branched chain, saturated hydrocarbon group. Further, alkyl groups are straight chain alkyls, e.g., in an embodiment, methyl, ethyl, n-propyl, n-butyl, n-pentyl, n-hexyl, or branched chain alkyl groups, e.g., —$CH(CH_3)_2$, —$CH(CH_2CH_3)_2$, —$C(CH_3)_3$, —$C(CH_2CH_3)_3$, —$CH(CH_3)(CH_2CH_3)$, —$CH_2CH(CH_3)_2$, —$CH_2CH(CH_3)(CH_2CH_3)$, —$CH_2CH(CH_2CH_3)_2$, —$CH_2C(CH_3)_3$, —$CH(CH_3)CH(CH_3)(CH_2CH_3)$, —$CH_2CH_2CH(CH_3)_2$, —$CH_2CH_2CH(CH_3)(CH_2CH_3)$, —$CH_2CH_2C(CH_3)_3$, or —$CH(CH_3)CH_2CH(CH_3)_2$. Accordingly, alkyl groups include primary alkyl groups, secondary alkyl groups, and tertiary alkyl groups. Further envisaged alkyl groups are lower alkyl groups, i.e., in an embodiment, alkyl groups with at most 6 carbon atoms, in a further embodiment with at most 3 carbon atoms, in a further embodiment with one carbon atom, i.e., methyl groups. In an embodiment, the alkyl is a straight-chain lower alkyl, in an embodiment selected from the list consisting of n-hexyl, n-pentyl, n-butyl, n-propyl, ethyl, and methyl. In an embodiment, $R^1$ and $R^2$ are independently selected from —H and $C_1$ to $C_3$ alkyl. In a further embodiment, $R^1$ and $R^2$ are independently selected from —H, ethyl, and methyl, in a further embodiment, at least one of $R^1$ and $R^2$ is methyl, in a further embodiment, both $R^1$ and $R^2$ are methyl.

In an embodiment, the polymer having —CO—$NR^1R^2$ side groups is obtained or obtainable from a composition comprising monomers as specified herein below, which is referred to herein as "monomer composition." In an embodiment, the polymer having —CO—$NR^1R^2$ side groups is obtained or obtainable from a composition comprising monomers of the general structure (I)

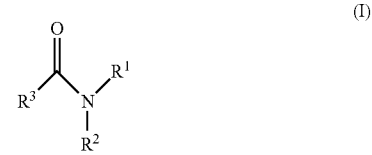

(I)

with $R^3$ being a polymerizable group. Suitable polymerizable chemical groups and methods for their polymerization are known in the art. In an embodiment, $R^3$ is selected from an $C_2$ to $C_4$ alkenyl group.

As used herein the term "alkenyl" relates to a hydrocarbon group formed when a hydrogen is removed from an alkene. In an embodiment, $R^3$ is selected from vinyl (i.e., ethenyl, —CH=$CH_2$), propenyl (—CH=CH—$CH_3$) and isopropenyl (—C($CH_3$)=$CH_2$). In a further embodiment, $R^3$ is vinyl; thus, in an embodiment, the polymer having —CO—$NR^1R^2$ side groups is obtained or obtainable from a monomer composition comprising acrylamide monomers, in an embodiment comprising mono- and/or di-N-substituted acrylamide monomers.

In an embodiment, the monomer composition comprises a multitude of non-identical monomers of the general structure (I) as specified above, e.g., at least two non-identical monomers of the general structure (I). In an exemplary embodiment, the monomer composition comprises acrylamide monomers and at least one type of mono- and/or di-N-substituted acrylamide monomer; or the monomer composition comprises least one type of mono- and/or di-N-substituted monomer wherein $R^1$ and/or $R^2$ are/is $C_1$ to $C_3$ alkyl, in an embodiment improving biocompatibility of the polymer, and at least one type of mono- and/or di-N-substituted monomer wherein $R^1$ and/or $R^2$ are/is $C_4$ to $C_6$ alkyl, in an embodiment improving mechanical properties of the polymer; or the monomer composition comprises least one type of mono- and/or di-N-substituted monomer wherein $R^1$ and $R^2$ are $C_1$ to $C_3$ alkyl, and at least one type of mono- and/or di-N-substituted monomer wherein $R^1$ and $R^2$ are $C_4$ to $C_6$-alkyl.

In an embodiment, the monomer composition as specified herein further comprises at least one further monomer not corresponding to the general structure (I). In an embodiment, such monomer is a monomer suitable for cross-linking and/or branching polymer chains. Both types of monomers are known in the art. Thus, in an embodiment, the monomer composition further comprises at least one monomer comprising a cross-linkable side group.

As used herein, the term "cross-linkable side group" relates to a chemically reactive or activatable group suitable for establishing a covalent bond from the molecule comprising said cross-linkable side group to a further chemical molecule or to a different part of the same molecule. In an embodiment, the cross-link is to a further molecule of the polymer or to the diffusion membrane as specified elsewhere herein. As is known in the art, cross-linking may be obtained by including a side group into a polymer which can be reacted with a chemically reactive group, or by including a chemically reactive or an activatable side group into the polymer. In an embodiment, the cross-linkable group is a side group comprising an —OH or —$NH_2$ group comprised in the polymer, which may be cross-linked by a multifunctional, in an embodiment bifunctional cross-linking agent known in the art, including, e.g., diglycidyl ethers like poly(ethylene glycol) diglycidyl ether and poly(propylene glycol) diglycidyl ether, bis-aldehydes, and succinimidyl esters. In a further embodiment, the cross-linkable side group is an activatable side group, i.e., a side group which is chemically essentially non-reactive under standard conditions and/or in the dark, but chemically reactive after activation, e.g., by illumination with an appropriate wavelength. In an embodiment, the cross-linkable side group is selected from the list consisting of benzophenones, aryl azides, azido-methyl-coumarins, anthraquinones, certain diazo compounds, diazirines, and psoralen derivatives. In a further embodiment, the cross-linkable side group is a benzophenone side group. In a further embodiment, the cross-linkable side group is an obtained or obtainable from O-substituted methacrylate monomers, in an embodiment from 4-Benzoylphenyl methacrylate monomers.

In an embodiment, the polymer having —CO—$NR^1R^2$ side groups is obtained or obtainable from a composition comprising mono-N- or di-N-substituted acrylamide monomers, in an embodiment comprising N,N-dimethyl-acrylamide monomers. In a further embodiment, the polymer having —CO—$NR^1R^2$ side groups is a copolymer, in an embodiment a statistical copolymer. In further embodiments, besides —CO—$NR^1R^2$, the copolymer comprises a further repeat-unit, which can provide additional function, such as crosslinking, improved biocompatibility, or mechanical property, as specified above.

In a further embodiment, the polymer having —CO—$NR^1R^2$ side groups is a copolymer of mono-N- or di-N-substituted acrylamide monomers and/or O-substituted methacrylate monomers. In a further embodiment, the polymer comprises a chemical structure as indicated in formula (II) or (IIa):

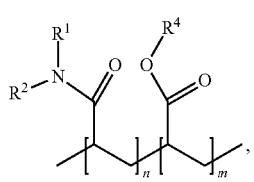

(II)

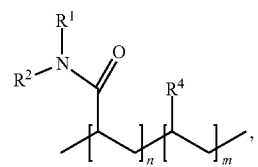

(IIa)

wherein $R^4$ is a cross-linkable side group, wherein n is from 0.01 to 0.99 and m is of from 0.99 to 0.01, in an embodiment wherein the sum of m and n is 1. In an embodiment, n is of from 0.5 to 0.99, m is of from 0.5 to 0.01, and the sum of m and n is 1. As is understood by the skilled person, the sum of m and n may be less than 1 in case other side-chains or side groups are comprised in the polymer; thus, in an embodiment, the sum of m plus n is at most 1; in an embodiment, the sum of m plus n is 1, i.e., the polymer only has side groups as shown in formula (II). In a further embodiment, the polymer has side groups as shown in formula IIa). As is also understood by the skilled person, the cross-linkable side group $R^4$ may also be a cross-linked side group, i.e., a cross-linkable side group after cross-linking, providing a covalent bond to a further molecule of the polymer or to a diffusion membrane.

In an embodiment, the polymer having —CO—$NR^1R^2$ side groups is a copolymer obtained or obtainable from a composition comprising the monomers of the general structure (I) as specified above and monomers comprising a cross-linkable side group, in an embodiment a benzophenone side group. In a further embodiment, the polymer having —CO—$NR^1R^2$ side groups comprises from 1 to 50 mol-%, in an embodiment from 2 to 25 mol-%, in a further embodiment from 3 to 10 mol-% of units derived from monomers comprising a cross-linkable side group based on the total amount of the polymer having —CO—$NR^1R^2$ side groups. In an embodiment, the polymer comprises a chemical structure as indicated in formula (III), (IIIa), (IIIb), and/or (IIIc):

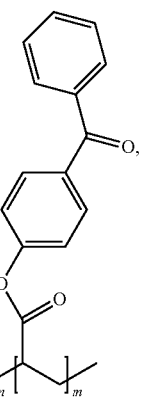

(III)

-continued

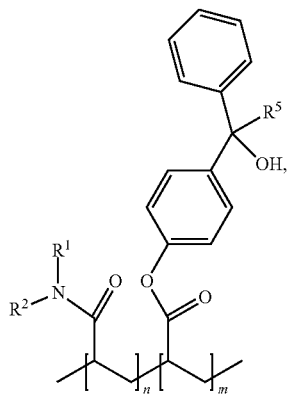

(IIIa)

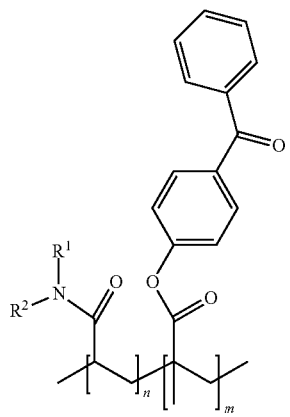

(IIIb)

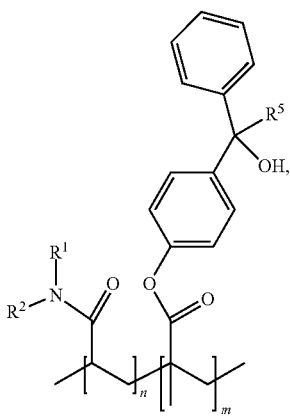

(IIIc)

wherein $R^5$ is a further polymer molecule or a molecule of a diffusion membrane.

In an embodiment, the polymer comprises a chemical structure as indicated in formula (III) or (IIIa). In an embodiment, the polymer comprises a chemical structure as indicated in formula (IIIb) or (IIIc).

Thus, in an embodiment, the polymer has a chemical structure as indicated in formula (IV), or (IVa)

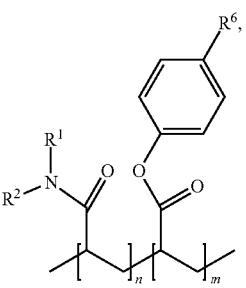

(IV)

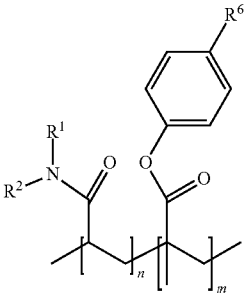

(IVa)

wherein n is from 0.01 to 0.99 and m is of from 0.99 to 0.01, and wherein $R^6$ is —CO—$C_6H_5$ (Benzoyl) or —C(OH)$R^5$—$C_6H_5$, with $R^5$ as specified herein above, in an embodiment wherein the sum of m and n is 1. In an embodiment, n is of from 0.5 to 0.99, m is of from 0.5 to 0.01, and the sum of m and n is 1.

In a further embodiment, the polymer having —CO—$NR^1R^2$ side groups is a terpolymer of at least two non-identical mono-N- or di-N-substituted acrylamide monomers as specified elsewhere herein and O-substituted methacrylate monomers, in an embodiment 4-Benzoylphenyl methacrylate monomers.

The term "analyte," as used herein, relates to a chemical compound present in a liquid, in particular a bodily liquid. In an embodiment, the analyte is an organic molecule, in a further embodiment, an organic molecule capable of undergoing a redox reaction in the presence of the enzyme according to this disclosure. In an embodiment, the analyte is a molecule of a subject's metabolism, i.e., a molecule produced by and/or consumed in at least one chemical reaction taking place in at least one tissue of said subject. Also in an embodiment, the analyte is a low molecular weight chemical compound, in a further embodiment, a chemical compound with a molecular mass of less than 5000 u (5000 Da; 1 u=1.66×10-27 kg), in a further embodiment, less than 1000 u, in a further embodiment, less than 500 u. I.e., in an embodiment, the analyte is not a biological macromolecule. In a further embodiment, the analyte is selected from the list consisting of glucose, malate, ethanol, ascorbic acid, cholesterol, glycerol, urea, 3-hydroxybutyrate, lactate, pyruvate, ketones, and creatinine; still in a further embodiment, the analyte is glucose.

The term "determining," as used herein, relates to the quantification of the amount of analyte present in a sample of a body fluid, i.e., measuring the amount or concentration of said analyte, in an embodiment semi-quantitatively or quantitatively. The detection of the amount of the analyte can be accomplished in a variety of ways known to the skilled person or detailed elsewhere herein. In accordance with this disclosure, detecting the amount of the analyte can be achieved by all known means for detecting the amount of said analyte in a sample. In an embodiment, determining is specifically detecting the analyte of this disclosure. In an embodiment, determining an analyte is in vivo determining said analyte, in a further embodiment, determining an analyte is continuous glucose monitoring, in a further embodiment, is continuous in vivo glucose monitoring, in a further embodiment in a subject as specified elsewhere herein.

The term "amount" as used herein encompasses the absolute amount of the analyte referred to herein, the relative amount or concentration of the analyte referred to herein as well as any value or parameter which correlates thereto. Such values or parameters comprise intensity signal values from all specific physical or chemical properties obtained from the analyte referred to herein by measurements. It is to be understood that values correlating to the aforementioned amounts or parameters can also be obtained by all standard mathematical operations.

As used herein, the term "body fluid" relates to all bodily fluids of a subject known to comprise or suspected to comprise the analyte of this disclosure, including interstitial fluid, blood, plasma, lacrimal fluid, urine, lymph, cerebrospinal fluid, bile, stool, sweat, and saliva. In an embodiment, the body fluid is interstitial fluid or blood; thus, in an embodiment, the body fluid comprises at least one particulate component, in particular cells. In a further embodiment, the body fluid is interstitial fluid. The term "sample" is understood by the skilled person and relates to any subportion of a bodily fluid, in an embodiment removed from the subject prior to applying said sample to a test element. Samples can be obtained by well known techniques including, e.g., venous or arterial puncture, epidermal puncture, and the like.

Advantageously, it was found in the work underlying this disclosure that the polymers described are particularly suitable as biocompatible coatings for biosensors. Surprisingly, it was found that the polymers described herein have a reduced tendency for fouling by accumulation of biological macromolecules and/or by adhesion of cells, have a low cytotoxicity and a low immune-activating activity. Thus, biosensors of this disclosure have an increased duration of usability and a low tendency for encapsulation.

The definitions made above apply mutatis mutandis to the following. Additional definitions and explanations made further below also apply for all embodiments described in this specification mutatis mutandis.

This disclosure further relates to a method for producing an implantable biosensor for determining an analyte, comprising at least partially coating said biosensor with a biocompatibility layer according to this disclosure.

Methods for producing polymer layers and coatings on biosensors and/or sensor modules are known in the art. As used herein, the process of coating can be achieved by any method deemed appropriate by the skilled person, including methods generating a coating in situ by applying a solution of monomers, preceded by, concomitant to, or followed by start of polymerization, as well as applying a pre-manufactured membrane to the biosensor. In an embodiment, the method for producing an implantable biosensor includes at least one of dip coating, spray coating, and contact coating. Further a method selected from dip coating, spray coating, spin coating, a pressing process, a knife process or a dropping process may be used. However, combinations of the stated methods and/or other methods can basically also be used. In an embodiment, the biocompatibility layer is produced on a diffusion membrane. In an embodiment, the method further comprises a step of crosslinking the biocompatibility layer to an underlying layer, in particular a diffusion membrane, e.g., by irradiation, e.g., at 365 nm. In an embodiment, the method for producing an implantable biosensor further comprises an additional step of extracting non-polymerized mono- and oligomers from the biocompatibility layer of the biosensor, e.g., by treating the biosensor with a solvent, e.g., an organic solvent and/or water.

This disclosure also relates to a use of a biocompatibility layer of this disclosure for producing an implantable biosensor.

This disclosure also relates to a use of a biosensor according to this disclosure for continuous in situ determination of an analyte. As specified elsewhere herein, the analyte, in an embodiment, is glucose.

Further, this disclosure relates to a method for continuous determination of an analyte in a subject, wherein said method comprises determining said analyte by means of the biosensor according to this disclosure.

Furthermore, this disclosure relates to a method for continuous determination of an analyte in a subject, said method comprising (a) implanting a biosensor according to this disclosure into at least one tissue of said subject; and (b) determining said analyte by means of said sensor.

The methods for continuous determination of an analyte of this disclosure, in an embodiment, are in vivo methods. Moreover, they may comprise steps in addition to those explicitly mentioned above. For example, further steps may relate, e.g., to providing an amount or concentration of an analyte based on the determination of said analyte, or providing an alert in case said analyte is determined to be below a first threshold value or above a second threshold value. Moreover, one or more of said steps may be performed by automated equipment. In an embodiment, said method does not comprises diagnosis of disease based on said measurement.

As used herein, the term "subject" relates to a vertebrate. In an embodiment, the subject is a mammal, in a further embodiment, a mouse, rat, cat, dog, hamster, guinea pig, sheep, goat, pig, cattle, or horse. Still in a further embodiment, the subject is a primate. In a further embodiment, the subject is a human. In an embodiment, the subject is afflicted or suspected to be afflicted with a disease or condition associated with a measurable deviation from normal of at least one analyte. In a further embodiment, the subject is afflicted with diabetes.

The term "continuous determination," as used herein, relates to determination of an analyte by repeated use of the same biosensor, in particular the biosensor disclosed herein, in a subject. Thus, the term continuous determination includes discrete measurements, in an embodiment measurements at least every 6 hours, in a further embodiment at least every 2 hours, in a further embodiment at least every hour. However, also more frequent measurements are encompassed by the term, in particular measurements at least every 30 min, in a further embodiment at least every 15 min, in a further embodiment at least every 10 min, in a further embodiment at least every 5 min. In an embodiment, the term relates to quasi-continuous measurement, in an embodiment every 30 s, in a further embodiment at least every 20 s, in a further embodiment at least every 10 s, in a further embodiment at least every 5 s. However, even more frequent measurements are envisaged as well. In an embodiment, continuous determination is determination for at least 1 week, in an embodiment at least 2 weeks, in a further embodiment at least 3 weeks, in a further embodiment at least 4 weeks using the same biosensor.

In view of the above, the following embodiments are particularly envisaged:

1. A biosensor for determining an analyte comprising a sensor module covered at least partially by a biocompatibility layer, wherein said biocompatibility layer comprises a polymer having —CO—NR$^1$R$^2$ side groups, wherein R$^1$ and R$^2$ are independently selected from —H and C$_1$ to C$_6$ alkyl, in an embodiment wherein at most one of R$^1$ and R$^2$ is —H.
2. The biosensor of embodiment 1, wherein R$^1$ and R$^2$ are independently selected from —H and C$_1$ to C$_3$ alkyl.
3. The biosensor of embodiment 1 or 2, wherein R$^1$ and R$^2$ are independently selected from —H, ethyl, and methyl.
4. The biosensor of any one of embodiments 1 to 3, wherein at least one of R$^1$ and R$^2$ is methyl.
5. The biosensor of any one of embodiments 1 to 4, wherein R$^1$ and R$^2$ are methyl.
6. The biosensor of any one of embodiments 1 to 5, wherein said polymer having —CO—NR$^1$R$^2$ side groups is obtained or obtainable from a composition comprising monomers of the general structure (I)

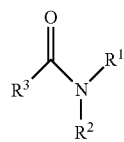
(I)

with R$^3$ being a polymerizable group, in an embodiment selected from vinyl, propenyl, and isopropenyl, in an embodiment wherein R$^3$ is vinyl.

7. The biosensor of any one of embodiments 1 to 6, wherein said polymer having —CO—NR$^1$R$^2$ side groups is obtained or obtainable from a composition comprising mono-N- and/or di-N-substituted acrylamide monomers, in an embodiment comprising N,N-dimethyl-acrylamide monomers.
8. The biosensor of any one of embodiments 1 to 7, wherein said polymer having —CO—NR$^1$R$^2$ side groups is a copolymer, in an embodiment a statistical copolymer.
9. The biosensor of any one of embodiments 1 to 8, wherein said polymer having —CO—NR$^1$R$^2$ side groups is a copolymer of mono-N- or di-N-substituted acrylamide monomers and/or O-substituted methacrylate monomers.
10. The biosensor of embodiment 9, wherein said O-substituted methacrylate monomers are 4-Benzoylphenyl methacrylate monomers.
11. The biosensor of any one of embodiments 1 to 10, wherein said polymer has a chemical structure as indicated in formula (II) or (IIa):

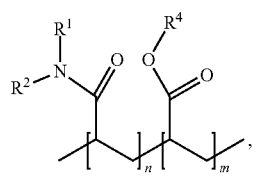
(II)

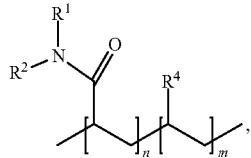
(IIa)

wherein R$^4$ is a cross-linkable or cross-linked side group, wherein n is from 0.01 to 0.99 and m is of from 0.99 to 0.01, in an embodiment wherein the sum of m and n is 1.

12. The biosensor of any one of embodiments 1 to 11, wherein n is of from 0.5 to 0.99, m is of from 0.01 to 0.5, and wherein the sum of m and n is 1.
13. The biosensor of any one of embodiments 1 to 12, wherein said polymer having —CO—NR$^1$R$^2$ side groups is a copolymer obtained or obtainable from a composition comprising the monomers as specified in embodiment 6 or 7 and monomers comprising a cross-linkable side group, in an embodiment a benzophenone side group.
14. The biosensor of any one of embodiments 1 to 13, wherein the polymer having —CO—NR$^1$R$^2$ side groups comprises from 1 to 50 mol-%, in an embodiment from 2 to 25 mol-%, in a further embodiment from 3 to 10 mol-% of units derived from monomers comprising a cross-linkable side group based on the total amount of the polymer having —CO—NR$^1$R$^2$ side groups.
15. The biosensor of any one of embodiments 1 to 14, wherein said polymer comprises a chemical structure as indicated in formula (III), (IIIa), (IIIb) and/or (IIIc):

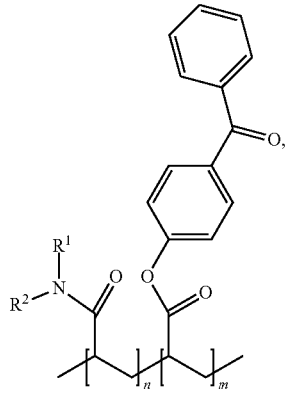
(III)

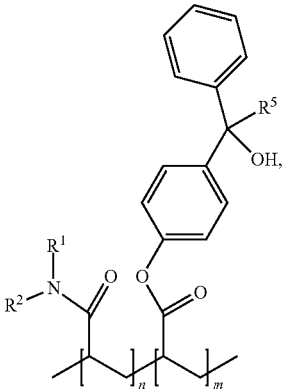
(IIIa)

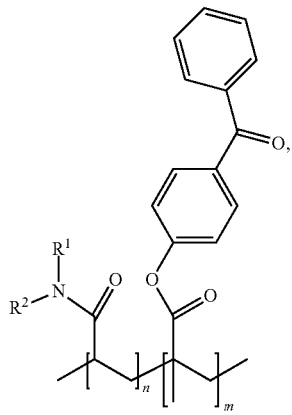

(IIIb)

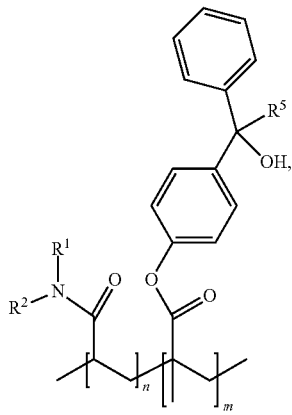

(IIIc)

wherein n is from 0.01 to 0.99 and m is of from 0.99 to 0.01, in an embodiment wherein the sum of m and n is 1; and wherein $R^5$ is a further polymer molecule or a molecule of a diffusion membrane.

16. The biosensor of any one of embodiments 1 to 15, further comprising a diffusion membrane, wherein said biocompatibility layer is the outmost layer.

17. The biosensor of any one of embodiments 1 to 16, further comprising a diffusion membrane, wherein said diffusion membrane comprises a hydrophilic polyurethane polymer.

18. The biosensor of any one of embodiments 1 to 17, wherein said biosensor is implantable, in an embodiment is implantable subcutaneously.

19. The biosensor of any one of embodiments 1 to 18, wherein said analyte is an analyte having a molecular weight of less than 1000 Da.

20. The biosensor of any one of embodiments 1 to 19, wherein said analyte is selected from the list consisting of glucose, malate, ethanol, ascorbic acid, cholesterol, glycerol, urea, 3-hydroxybutyrate, lactate, pyruvate, ketones, and creatinine, in an embodiment, the analyte is glucose.

21. The biosensor of any one of embodiments 1 to 20, wherein said determining an analyte is in vivo determining said analyte.

22. The biosensor of any one of embodiments 1 to 21, wherein said determining an analyte is continuous glucose monitoring.

23. A method for producing an implantable biosensor for determining an analyte, comprising at least partially coating said biosensor with a biocompatibility layer, wherein said biocompatibility layer comprises a polymer having —CO—NR$^1$R$^2$ side groups, wherein $R^1$ and $R^2$ are independently selected from —H and $C_1$ to $C_6$ alkyl, in an embodiment wherein at most one of $R^1$ and $R^2$ is —H.

24. The method of embodiment 23, wherein $R^1$ and $R^2$ are independently selected from —H and $C_1$ to $C_3$ alkyl.

25. The method of embodiment 23 or 24, wherein $R^1$ and $R^2$ are independently selected from —H, ethyl, and methyl.

26. The method of any one of embodiments 23 to 25, wherein at least one of $R^1$ and $R^2$ is methyl.

27. The method of any one of embodiments 23 to 26, wherein $R^1$ and $R^2$ are methyl.

28. The method of any one of embodiments 23 to 27, wherein said polymer having —CO—NR$^1$R$^2$ side groups is obtained or obtainable from a composition comprising monomers of the general structure (I)

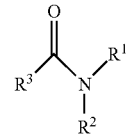

(I)

with $R^3$ being a polymerizable group, in an embodiment selected from vinyl, propenyl and isopropenyl, in an embodiment wherein $R^3$ is vinyl.

29. The method of any one of embodiments 23 to 28, wherein said polymer having —CO—NR$^1$R$^2$ side groups is obtained or obtainable from a composition comprising mono-N- and/or di-N-substituted acrylamide monomers, in an embodiment comprising N,N-dimethyl-acrylamide monomers.

30. The method of any one of embodiments 23 to 29, wherein said polymer having —CO—NR$^1$R$^2$ side groups is a copolymer, in an embodiment a statistical copolymer.

31. The method of any one of embodiments 23 to 30, wherein said polymer having —CO—NR$^1$R$^2$ side groups is a copolymer of mono-N- or di-N-substituted acrylamide monomers and/or O-substituted methacrylate monomers.

32. The method of embodiment 31, wherein said O-substituted methacrylate monomers are 4-Benzoylphenyl methacrylate monomers.

33. The method of any one of embodiments 23 to 32, wherein said polymer has a chemical structure as indicated in formula (II) or (IIa):

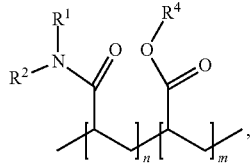

(II)

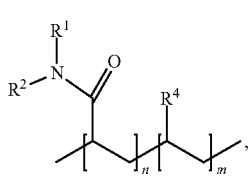

wherein R⁴ is a cross-linkable side group, wherein n is from 0.01 to 0.99 and m is of from 0.99 to 0.01, in an embodiment wherein the sum of m and n is 1.

34. The method of any one of embodiments 23 to 33, wherein n is of from 0.5 to 0.99, m is of from 0.5 to 0.01, and wherein the sum of m and n is 1.
35. The method of any one of embodiments 23 to 34, wherein said polymer having —CO—NR¹R² side groups is a copolymer obtained or obtainable from a composition comprising the monomers as specified in embodiment 28 or 29 and monomers comprising a cross-linkable side group, in an embodiment a benzophenone side group.
36. The method of any one of embodiments 23 to 35, wherein the polymer having —CO—NR¹R² side groups comprises from 1 to 50 mol-%, in an embodiment from 2 to 25 mol-%, in a further embodiment from 3 to 10 mol-% of units derived from monomers comprising a cross-linkable side group based on the total amount of the polymer having —CO—NR¹R² side groups.
37. The method of any one of embodiments 23 to 36, wherein said polymer comprises a chemical structure as indicated in formula (III), (IIIa), (IIIb), and/or (IIIc):

(III)

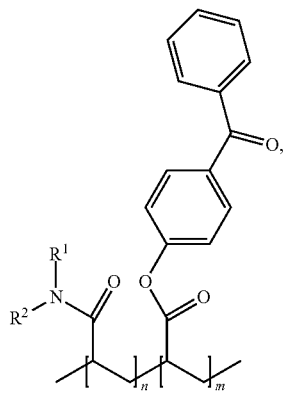

(IIIa)

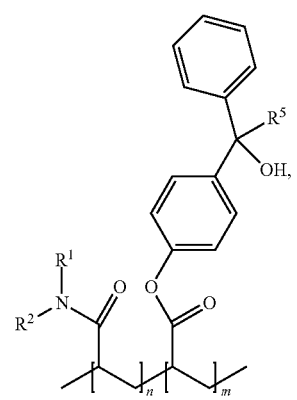

(IIIb)

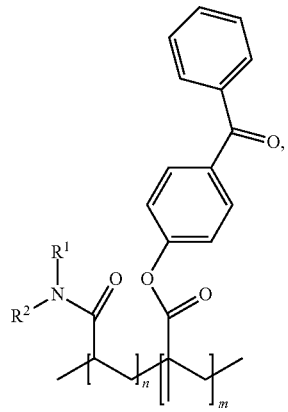

(IIIc)

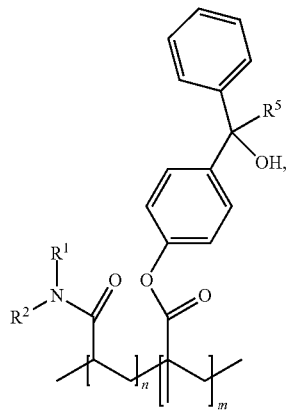

wherein n is from 0.01 to 0.99 and m is of from 0.99 to 0.01, in an embodiment wherein the sum of m and n is 1.

38. The method of any one of embodiments 1 to 37, further comprising at least partially coating said biosensor with a diffusion membrane, wherein said biocompatibility layer is the outmost layer.
39. The method of embodiment 38, wherein said diffusion membrane comprises a hydrophilic polyurethane polymer.
40. Use of a biocompatibility layer for producing an implantable biosensor, wherein said biocompatibility layer comprises a polymer having —CO—NR¹R² side groups, wherein R¹ and R² are independently selected from —H and C₁ to C₆ alkyl, in an embodiment wherein at most one of R¹ and R² is —H.
41. The use of embodiment 40, wherein R¹ and R² are independently selected from —H and C₁ to C₃ alkyl.
42. The use of embodiment 40 or 41, wherein R¹ and R² are independently selected from —H, ethyl, and methyl.
43. The use of any one of embodiments 40 to 42, wherein at least one of R¹ and R² is methyl.
44. The use of any one of embodiments 40 to 43, wherein R¹ and R² are methyl.
45. The use of any one of embodiments 40 to 44, wherein said polymer having —CO—NR¹R² side groups is obtained or obtainable from a composition comprising monomers of the general structure (I)

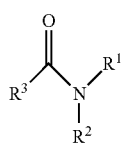
(I)

with R³ being a polymerizable group, in an embodiment selected from vinyl, propenyl and isopropenyl, in an embodiment wherein R³ is vinyl.

46. The use of any one of embodiments 40 to 45, wherein said polymer having —CO—NR¹R² side groups is obtained or obtainable from a composition comprising mono-N- and/or di-N-substituted acrylamide monomers, in an embodiment comprising N,N-dimethylacrylamide monomers.
47. The use of any one of embodiments 40 to 46, wherein said polymer having —CO—NR¹R² side groups is a copolymer, in an embodiment a statistical copolymer.
48. The use of any one of embodiments 40 to 47, wherein said polymer is a linear polymer.
49. The use of any one of embodiments 40 to 48, wherein said polymer having —CO—NR¹R² side groups is a copolymer of mono-N- or di-N-substituted acrylamide monomers and/or O-substituted methacrylate monomers.
50. The use of embodiment 49, wherein said O-substituted methacrylate monomers are 4-Benzoylphenyl methacrylate monomers.
51. The use of any one of embodiments 40 to 50, wherein said polymer has a chemical structure as indicated in formula (II) or (IIa):

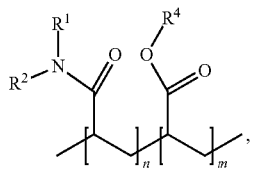
(II)

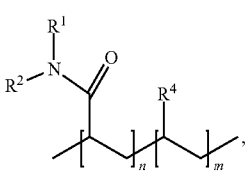
(IIa)

wherein R⁴ is a cross-linkable side group, wherein n is from 0.01 to 0.99 and m is of from 0.99 to 0.01, in an embodiment wherein the sum of m and n is 1.

52. The use of any one of embodiments 40 to 51, wherein n is of from 0.5 to 0.99, m is of from 0.5 to 0.01, and wherein the sum of m and n is 1.
53. The use of any one of embodiments 40 to 52, wherein said polymer having —CO—NR¹R² side groups is a copolymer obtained or obtainable from a composition comprising the monomers as specified in embodiment 45 or 46 and monomers comprising a cross-linkable side group, in an embodiment a benzophenone side group.
54. The use of any one of embodiments 40 to 53, wherein the polymer having —CO—NR¹R² side groups comprises from 1 to 50 mol-%, in an embodiment from 2 to 25 mol-%, in a further embodiment from 3 to 10 mol-% of units derived from monomers comprising a cross-linkable side group based on the total amount of the polymer having —CO—NR¹R² side groups.
55. The use of any one of embodiments 40 to 54, wherein said polymer comprises a chemical structure as indicated in formula (III), (IIIa), (IIIb) and/or (IIIc):

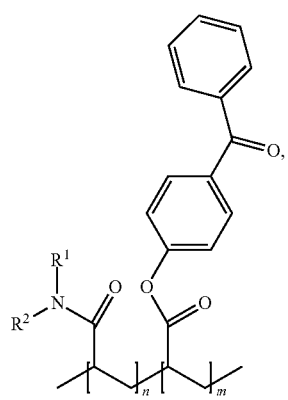
(III)

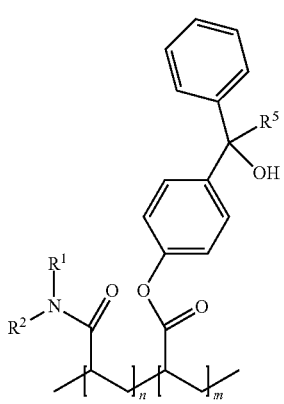
(IIIa)

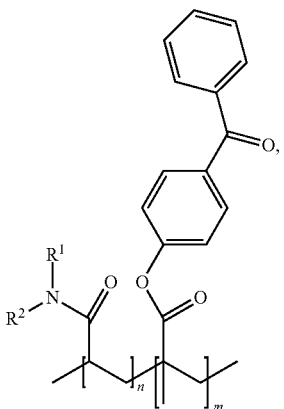
(IIIb)

-continued

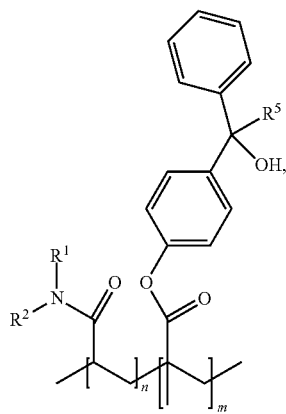

(IIIc)

wherein n is from 0.01 to 0.99 and m is of from 0.99 to 0.01, in an embodiment wherein the sum of m and n is 1.

56. Use of a biosensor according to any one of embodiments 1 to 55 for continuous in situ determination of an analyte.
57. A method for continuous determination of an analyte in a subject, wherein said method comprises determining said analyte by means of the biosensor according to any one of embodiments 1 to 22.
58. A method for continuous determination of an analyte in a subject, said method comprising
(a) implanting a biosensor according to any one of embodiments 1 to 22 into at least one tissue of said subject; and
(b) determining said analyte by means of said sensor.
59. The method of embodiment 57 or 58, wherein said continuous determination is determination for at least 1 week, in an embodiment at least 2 weeks, in a further embodiment at least 3 weeks, in a further embodiment at least 4 weeks using the same biosensor.

All references cited in this specification are herewith incorporated by reference with respect to their entire disclosure content and the disclosure content specifically mentioned in this specification.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1B:
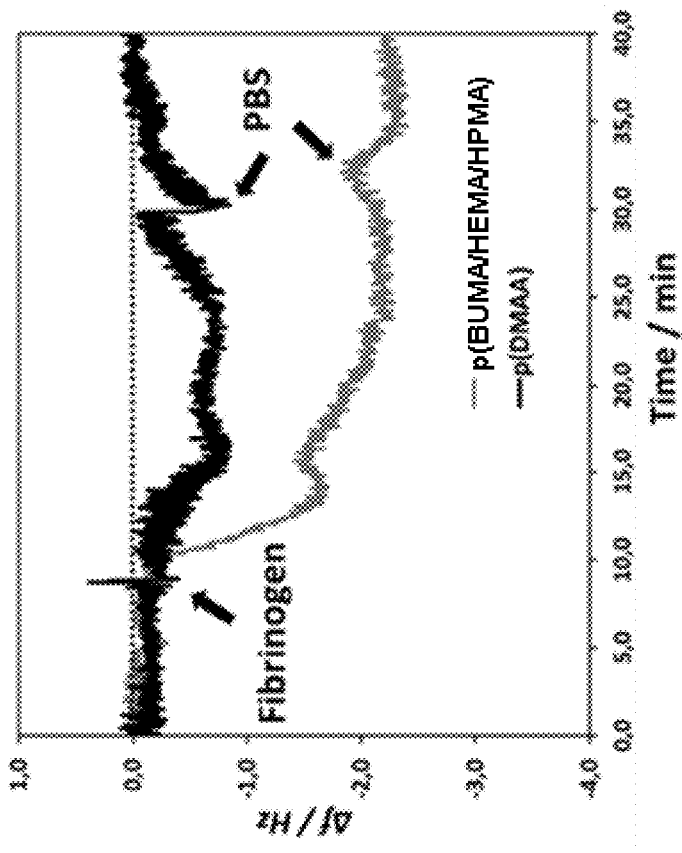
FIGS. 1A and 1B show protein-adsorption studies in QCM experiments.
Figure 1A:
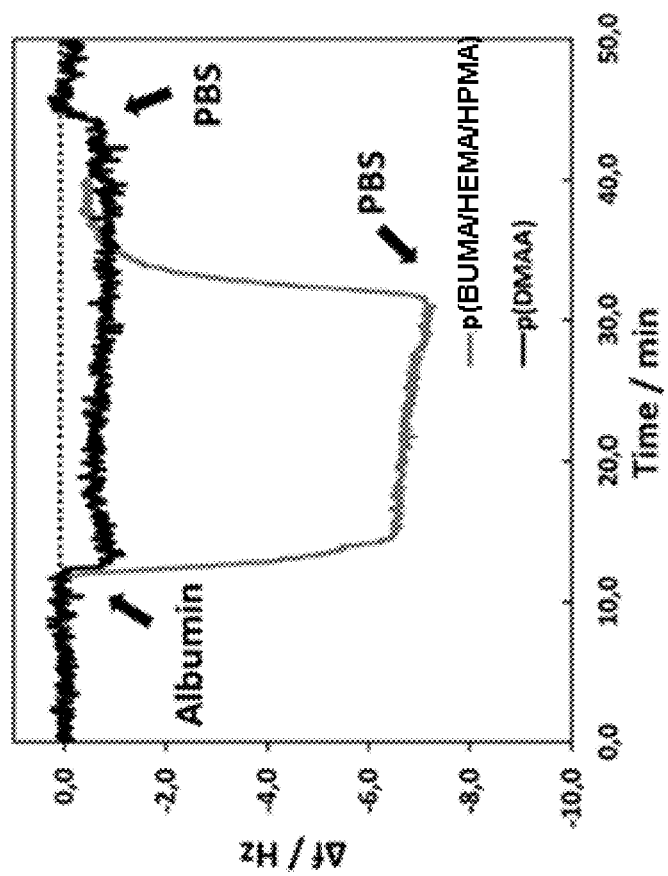

FIGS. 1A and 1B: Protein-adsorption study in QCM experiments. The frequency change ($\Delta f$, [Hz]) is plotted against time [min]; time points of protein addition and buffer wash(es) are indicated by arrows. a) The lower curves at 20 min are the curves representing the experiments using p(BUMA/HEMA/HPMA), the upper curves at 20 min are the curves representing the experiments using p(DMAA); Test proteins were (FIG. 1A) albumin and (FIG. 1B) fibrinogen.

Figure 2B:
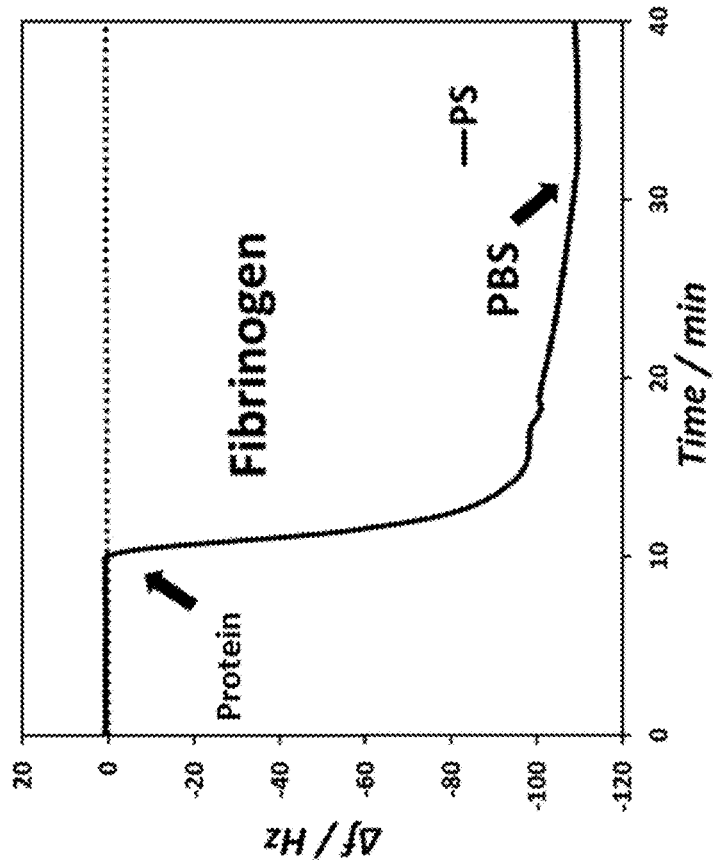
FIGS. 2A and 2B show protein of adsorption study of polystyrene in QCM experiments.
Figure 2A:
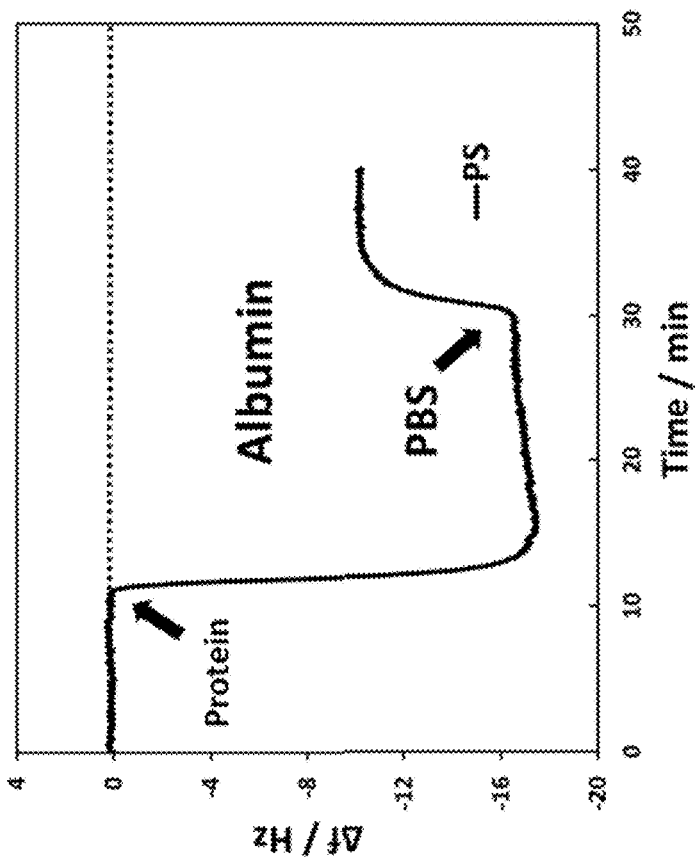

FIGS. 2A and 2B: Protein-adsorption study of Polystyrene (PS) in QCM experiments. Test proteins were albumin (FIG. 2A) and fibrinogen (FIG. 2B).

Figure 3:
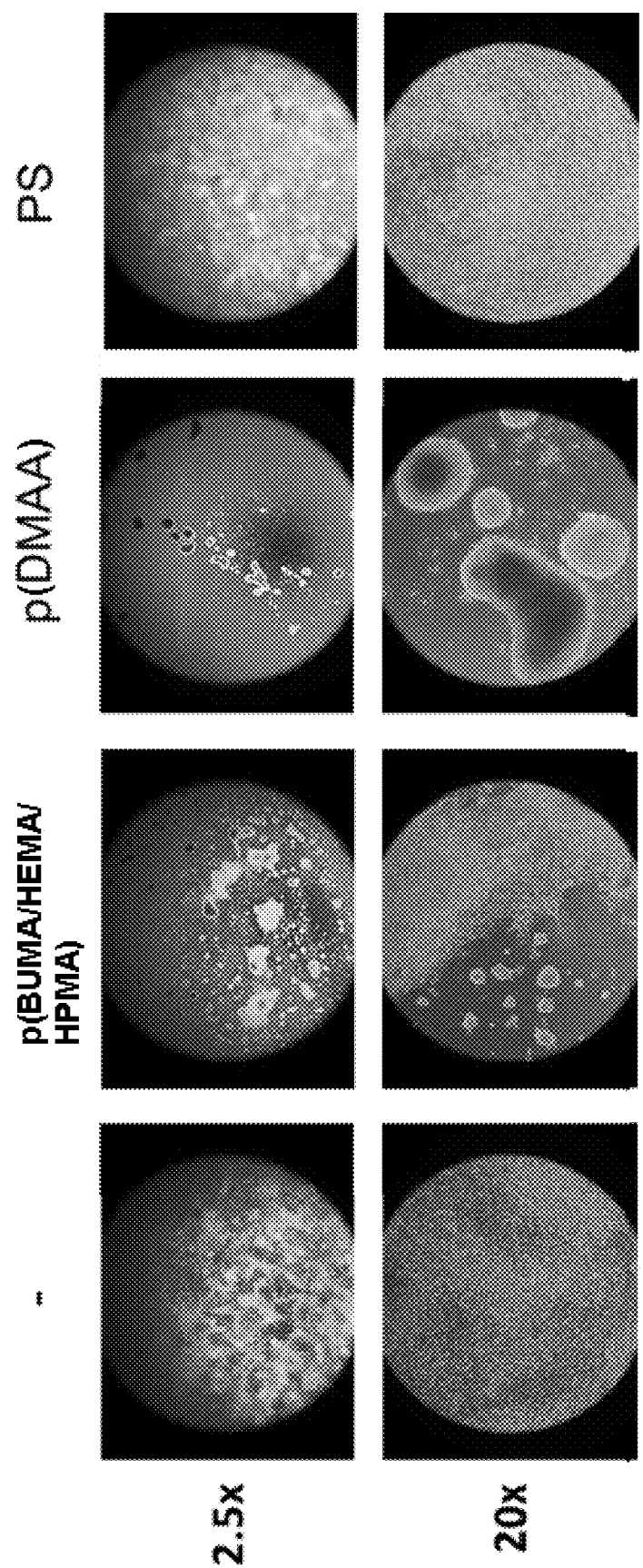
FIG. 3 shows cell-adhesion tests.

FIG. 3: Cell-adhesion tests on unfunctionalized glass surface (−), glass substrate functionalized with p(BUMA/HEMA/HPMA) polymer, glass substrate functionalized with p(DMAA) network (p(DMAA)), or polystyrene (PS) after 20 days incubation time. Magnification was 2.5× or 20×. The cells visible at 20× magnification with p(DMAA) are cell lumps not adhering to the substrate.

Figure 4:
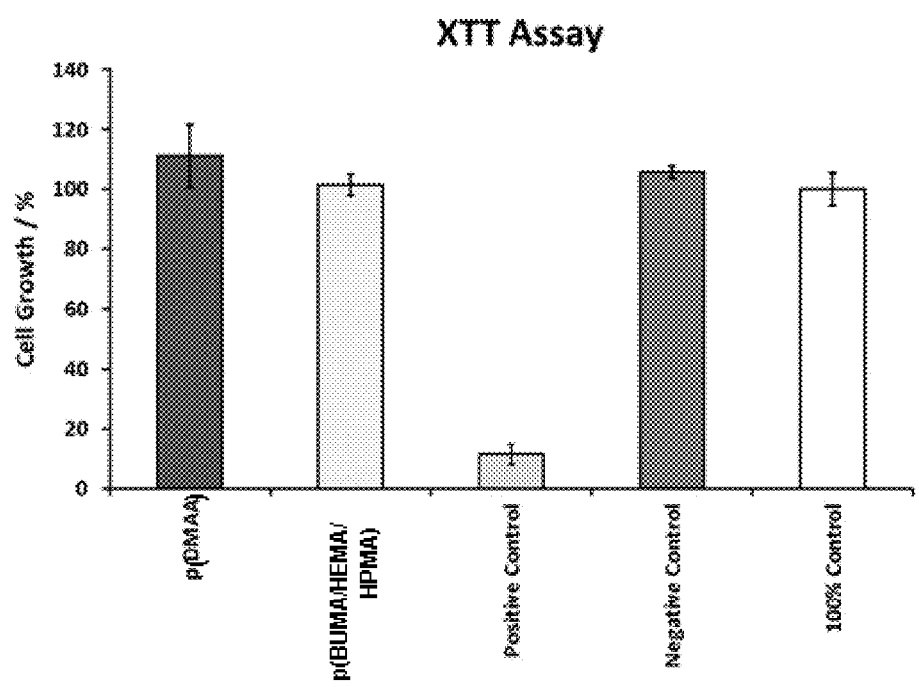
FIG. 4 shows percentage cell growth relative to a reference.

FIG. 4: Percentage cell growth relative to reference (Medium) determined in an 3-(4,5-dimethylthiazol-2-yl)-2,5-diphenyltetrazolium (MTT) assay, or a 2,3-bis-(2methoxy-4-nitro-5-sulfophenyl)-2H-tetrazolium-5-carboxanilide (XTT) assay, after 24 h incubation with extracts from p(DMAA)-coated samples (p(DMAA)), p(BUMA/HEMA/HPMA)-coated samples, or pieces of latex. Untreated cell-culture medium were used as 100% control. Pieces of latex were used as positive control, and PET substrates without coating were used as negative control.

Figure 5:
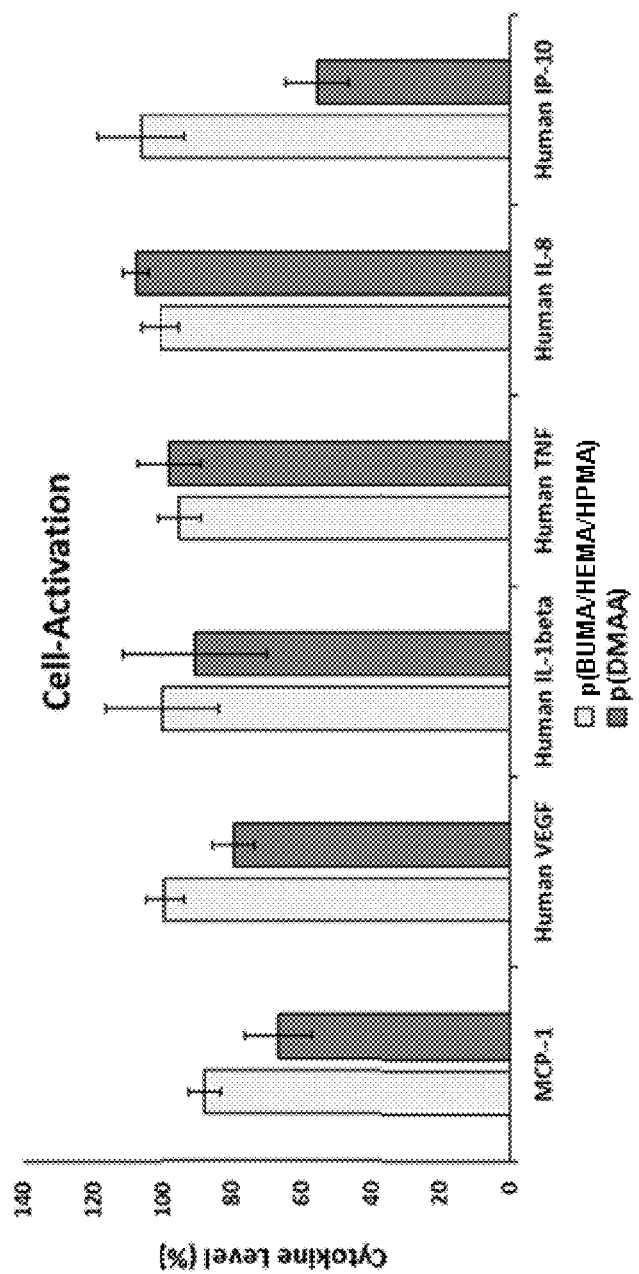
FIG. 5 shows relative cytokine production by THP-1 cells.

FIG. 5: Relative cytokine production by THP-1 cells contacting fibrinogen activated by p(BUMA/HEMA/HPMA)-coated Polyethyleneterephthalate (PET) or by p(DMAA)-coated PET. Uncoated PET was used as negative control, Fibrinogen coated directly onto PET was used as a reference (100%). PET substrates directly coated with fibrinogen were used as a reference (100%).

EXAMPLES

The following Examples shall merely illustrate this disclosure. They shall not be construed, whatsoever, to limit the scope of the invention.

Reagents Used in Examples p(BUMA/HEMA/HPMA): Copolymer of Hydroxyethylmethacrylate, Hydroxypropylmeth-acrylate, and Butylmethacrylate having a molar ratio of 90:5:5; PS: Polystyrene; p(DMAA): Copolymer of 97% dimethyl acrylamide and 3% benzophenone methacrylate; Latex: ACCUTech LOT 1307530704; phosphate buffered saline (PBS) buffer solution (Dulbecco's Phosphate buffered saline w/o Calcium or Magnesium available by Lonza (BE17-512F); 0.2 g/l KCl, 0.2 g/l $KH_2PO_4$, 8.0 g/l NaCl, 2.16 g/l $Na_2HPO_4 \cdot 7 H_2O$); sterile physiological saline solution (SPSS).

Protein Solutions: Albumin solution: 10 mg/mL in PBS buffer; Fibrinogen solution: 0.5 mg/mL in a mixture of PBS:SPSS=1:1.

Cells and cell growth medium: L-929 fibroblast cells (ATCC® CCL-1™); maintained in RPMI-Medium 1640 GlutaMAX (Gibco 72400-021), supplemented with 10% FCS (Sigma F7524), 1% Na-Pyruvate (Gibco 11360-070), and 1% Penicillin-Streptomycin (Gibco 15140-122).

XTT assay: Cells were adjusted to a density of approx. $10^5$ /mL; of this suspension, 100 μL were used per well of a 96 well plate.

Example 1: Protein-Adsorption

Protein adsorption by polymer layers was studied with quartz crystal microbalance (QCM) experiments using a Q-Sense QSX301 device. In these experiments, QCM substrates (Q-Sense) were first coated with a polymer or a polymer-network. The coated samples were placed into the measuring cell and induced to vibrate. The resonance vibration frequency was recorded. Then, the sample surface was covered with a PBS buffer solution and the polymer coating began to swell until it came to an equilibrium state, by which the resonance vibration frequency changed no more. Then, the protein-adsorption experiment was started by recording the vibration frequency again, recording the end resonance vibration frequency in buffer solution. After about 15 min the sample surface was further covered with the buffer solution, a protein solution was added into the measuring cell and allowed to cover the sample surface for ca. 15 min, after which the surface was washed again with the buffer solution to remove unattached proteins. The adsorbed proteins on the sample surface caused a reduction of frequency, and this reduction correlates with the amount of adsorbed proteins. For our experiments, the p(BUMA/HEMA/HPMA) polymer was coated directly onto the QCM substrate surface. For functionalization with p(DMAA) network, a polystyrene layer was first coated on the substrate, onto which the p(DMAA) was coated via spin-coating and then immobilized as a network by UV irradiation.

The results of the protein-adsorption experiments for p(BUMA/HEMA/HPMA) and p(DMAA) network are shown in FIGS. 1 and 2. Addition of albumin solution to the surface resulted in a significant frequency reduction of the p(BUMA/HEMA/HPMA)-coated surface. Most of this reduction could be recovered by washing the surface with buffer, but the frequency would not revert to baseline, indicating that a small amount of protein was irreversibly adsorbed on the p(BUMA/HEMA/HPMA)-coated surface. Much less frequency reduction was observed after adding albumin solution to the p(DMAA) surface and this could be completely recovered by washing with buffer. For fibrinogen adsorption, the frequency decrease caused by adding protein solution to the p(BUMA/HEMA/HPMA)-coated surface could not be reverted by washing with buffer, and the adsorbed proteins caused a frequency reduction of 2 Hz. On the other hand, similar to albumin, the frequency of the sample coated with p(DMAA) decreased only slightly after the surface was exposed to the protein solution. The frequency could be reverted back to baseline by removing the proteins with buffer. Thus, the p(DMAA) network showed improved resistance against albumin as well as fibrinogen adsorption.

Example 2: Cell Adhesion

Cell adhesion was tested on glass cover slips as substrates. The cover slips consisted of quartz glass and had a round shape with a diameter of 1.5 cm (VWR,ECN631-1579). Cover slips were stored between the respective steps of the experiment singly in 24 well plates, pointing the coating upward, and in a low-dust and low-germ environment. Cover slips were handled with a vacuum forceps. The surface of the cover slips was coated with p(BUMA/HEMA/HPMA) directly via spin coating; for p(DMAA) coating, the cover slip surface first was coated with polystyrene (PS) by spin coating, followed by coating with p(DMAA) by spin coating, again followed by UV irradiation (365 nm, 0,35 W/m$^2$, 2 min). Cover slips without coating and with PS only coating were used as controls.

To avoid microbial contamination of cells, the coated cover slips were sterilized by dipping into 70% ethanol/water or Perform (25% ethanol, 35% Propan-1-ol and 40% water) for 15 seconds, and by handling the cover slips in a sterile hood. After drying off sterilizing solution, cover slips were placed into wells of a 24 well plate containing 500 µL cell growth medium. Air bubbles underneath the cover slips were avoided by pressing the coverslips to the bottom of the well with forceps. Before use, the coated cover slips were left to swell for approximately one hour in cell growth medium.

L929 cells were cultured in a T75 bottle or flask up to 90% confluency. Cells were detached from the culture bottle by washing with Dulbecco's phosphate-buffered saline (DPBS), followed by addition of 1 mL trypsin/EDTA. Cells were trypsinized for approximately five minutes at 37° C., after which time 9 mL medium were added. Cells were carefully resuspended and centrifuged for two minutes at 500× g. The cell pellet was resuspended in 5 mL fresh medium (first with a 10 mL serological pipet, followed by resuspending with a 1 mL Eppendorf pipet). Cell density was adjusted by diluting 2 mL resuspended cells with 73 mL cell growth medium; of the adjusted suspension, 1 mL each was placed onto the cover slips, such that approximately 30,000 cells were applied per well. After seeding, cells were cultured in a standard $CO_2$ incubator.

The results of this experiment after 20 days incubation time are shown in FIG. 3. As can be seen, the unfunctionalized glass substrate surface was completely, e.g., confluently, covered with a cell layer, indicating that this surface has no resistance against cell adhesion. On the surface coated with p(BUMA/HEMA/HPMA), the cells could not adhere in the first 3 days. After longer incubation time, some of the cells could successfully attach irreversibly to the surface and started to grow and proliferate. After 20 days, most part of the p(BUMA/HEMA/HPMA) surface was covered by the cells (FIG. 3). No significant cell adhesion was observed on the surface coated with p(DMAA) network. The cells could only attach to each other after 20 days and formed cell lumps. When gently moving the samples, it was observed that the cell lumps floated and could not attach to the surface coated with p(DMAA) network. The results of this experiment showed that the surface coated with p(DMAA) network had strong resistance against cell adhesion.

Example 3: Toxicity Test

For the toxicity test, both sides of a PET substrate (2*2 cm) were coated with p(DMAA) network by spin coating with p(DMAA), followed by UV irradiation. The samples were sterilized with e-beam (25 kGy) before use. Three testing samples were immersed in 4 mL cell-culture medium for 24 h at 37° C. 1 mL of the incubated cell-culture medium (eluate) was transferred to a well of a fresh 96 well-plate, and L929 fibroblast cells were added and incubated for another 24 h, after which the survival rate of the cells was measured using the XTT-Test. The results are shown as percentage cell growth, using untreated cell-culture medium as a reference, (e.g., 100%). Thus, the lower the percentage growth value, the stronger is the toxic effect of the sample in the cells. Pieces cut from latex gloves and eluates prepared as above from PET substrates coated with p(BUMA/HEMA/HPMA) were used as controls, e.g., pieces cut from latex gloves were used as a positive control, and PET substrates without coating were used as negative control. As shown in FIG. 4, the p(DMAA) coating showed no detectable toxicity on L929 cells.

Example 4: Cell Activation by Fibrinogen-Coated Polymers

To test for a pro-inflammatory potential of polymers, human cell line THP-1 was used. THP-1 cells are monocyte-like cells which can be activated by exogenous stimuli, which cause the cells to increase secretion of cytokines into the culture medium. This activation can be induced directly by surface contact with the inducing material or by soluble components released from the material. A further option is activation of the cells by fibrinogen activated by contact with the surface of a polymer. This activation of fibrinogen causes a change in conformation exposing binding sites which bind to immune receptors on THP-1 cells, thereby causing activation of the cells. A still further option is activation of the cells on the coating surface by fibrinogen adsorption. This surface attachment causes a conformational change in fibrinogen through which the binding sites become exposed and are able to bind to immune receptors on THP-1 cells, thereby causing activation of the cells.

In the experiment, small PET plate substrates were coated with polymer (p(BUMA/HEMA/HPMA) or p(DMAA)) on one side. Coating with fibrinogen was performed by adding a solution of 2 mg/mL fibrinogen to the substrates and incubation at 37° C. for 16 hours. Surplus fibrinogen solution was removed and THP-1 cells were added. After 48 hours incubation at 37° C. in an incubator, the supernatant was separated from the cells and cytokines released into the supernatant were analyzed. Cytokine analysis was performed with the "Cytometric Bead Array (CBA)" assay kits from BD bioscience (Human Chemokine Kit and Human Inflammatory Cytokine Kit, both according to instructions by the manufacturer). Substrates coated with fibrinogen only were used as a reference.

The cytokine levels observed on the p(BUMA/HEMA/HPMA) and the p(DMAA) surfaces were normalized against the cytokine levels on control surface and are shown as percentage in FIG. 5. Samples coated with p(BUMA/HEMA/HPMA) and p(DMAA) showed comparable results for the activation of human IL-1beta, human TNF, and Human IL-8. Furthermore, the production of cytokines MCP-1, human VEGF was slightly lower on the p(DMAA) surface than the on the p(BUMA/HEMA/HPMA) surface. Interestingly, the p(DMAA) surface showed a significantly lower human IP-10 level than the p(BUMA/HEMA/HPMA) surface. The results of this test indicated that, compared to p(BUMA/HEMA/HPMA), the surface coated with p(DMAA) network shows improved biocompatibility.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A biosensor for determining an analyte, comprising:
a sensor module covered at least partially by a biocompatibility layer;
said biocompatibility layer comprises a polymer having —CO—NR$^1$R$^2$ side groups;
wherein 1e and 1e are independently selected from —H and $C_1$ to $C_6$ alkyl; and
wherein said polymer comprises a chemical structure as indicated in formula (II) or (IIa):

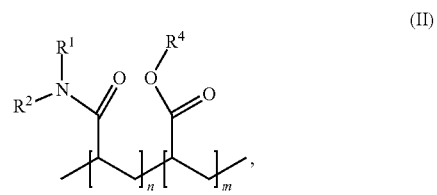

(II)

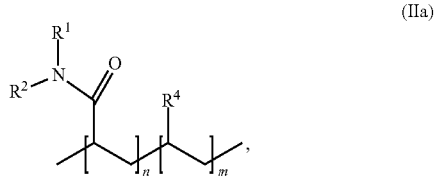

(IIa)

wherein $R^4$ is at least one cross-linkable or a cross-linked side group selected from the group consisting of: $(C_6H_5)_2CO$, and $(C_6H_5)_2COHR^5$;
wherein n is from 0.95 to 0.97 and m is from 0.03 to 0.05; and
wherein $R^5$ is a further polymer molecule or a molecule of a diffusion membrane.

2. The biosensor of claim 1, wherein $R^1$ and $R^2$ are independently selected from —H and $C_1$ to $C_3$ alkyl.

3. The biosensor of claim 1, wherein $R^1$ and $R^2$ are independently selected from methyl, —H, and ethyl.

4. The biosensor of claim 1, wherein $R^1$ and $R^2$ are methyl.

5. The biosensor of claim 1, wherein said polymer having —CO—NR$^1$R$^2$ side groups is obtained or obtainable from a composition comprising monomers of the general structure (I):

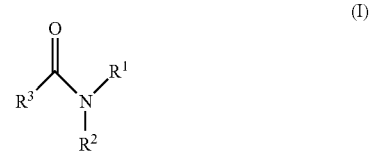

(I)

with $R^3$ being a polymerizable group.

6. The biosensor of claim 5, wherein $R^3$ is selected from vinyl, propenyl and isopropenyl.

7. The biosensor of claim 5, wherein $R^3$ is vinyl.

8. The biosensor of claim 1, wherein said polymer having —CO—NR$^1$R$^2$ side groups is a copolymer.

9. The biosensor of claim 8, wherein the copolymer is a statistical copolymer.

10. The biosensor of claim 1, wherein said polymer having —CO—NR$^1$R$^2$ side groups is a copolymer of mono-N- or di-N-substituted acrylamide monomers and/or O-substituted methacrylate monomers.

11. The biosensor of claim 10, wherein the O-substituted methacrylate monomers are 4-Benzoylphenyl methacrylate monomers.

12. The biosensor of claim 1, wherein said biosensor is implantable.

13. The biosensor of claim 1, wherein said biosensor is implantable subcutaneously.

14. The biosensor of claim 1, wherein said analyte is selected from the group consisting of glucose, malate, ethanol, ascorbic acid, cholesterol, glycerol, urea, 3-hydroxybutyrate, lactate, pyruvate, ketones, and creatinine.

15. The biosensor of claim 1, wherein said analyte is glucose.

16. A method for producing an implantable biosensor for determining an analyte, comprising at least partially coating said biosensor with a biocompatibility layer as claimed in claim 1.

17. A method for continuous determination of an analyte in a subject, wherein said method comprises determining said analyte by means of the biosensor according to claim 1.

18. The method of claim 17, wherein said continuous determination has a duration of at least 1 week with the same biosensor.

19. The method of claim 17, wherein said continuous determination has a duration of at least 2 weeks with the same biosensor.

20. The method of claim 17, wherein said continuous determination has a duration of at least 3 weeks with the same biosensor.

21. The method of claim 17, wherein said continuous determination has a duration of at least 4 weeks with the same biosensor.

22. The biosensor according to claim 1, wherein; n is 0.97; m is 0.03; and R$^1$ and R$^2$ are CH$_3$.

23. The biosensor according to claim 1, wherein said polymer comprises a chemical structure indicated in formula III and/or III(a):

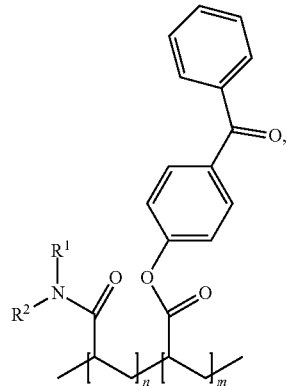

(III)

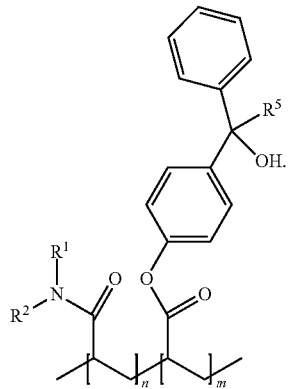

(IIIa)

* * * * *

UNITED STATES PATENT AND TRADEMARK OFFICE
CERTIFICATE OF CORRECTION

PATENT NO. : 11,925,460 B2
APPLICATION NO. : 17/003258
DATED : March 12, 2024
INVENTOR(S) : Peng Zou It is certified that error appears in the above-identified patent and that said Letters Patent is hereby corrected as shown below:

In the Claims

Claim 1, Column 28, Line 1, the phrase "wherein le and le are independently selected from –H" should read -- wherein $R^1$ and $R^2$ are independently selected from -H --.

Signed and Sealed this
Thirtieth Day of July, 2024

*Katherine Kelly Vidal*
*Director of the United States Patent and Trademark Office*